United States Patent [19]

Brownhill et al.

[11] 4,289,513
[45] Sep. 15, 1981

[54] ACTIVATED SORBTION PAPER AND PRODUCTS PRODUCED THEREBY

[75] Inventors: Richard D. Brownhill; Darcy B. Wilkinson, Jr., both of Lee, Mass.

[73] Assignee: The Mead Corporation, Dayton, Ohio

[21] Appl. No.: 890,181

[22] Filed: Mar. 27, 1978

[51] Int. Cl.³ .................. B01D 53/02; B01D 53/04
[52] U.S. Cl. .................................. 55/387; 55/521; 55/527; 55/528; 162/158; 428/131; 428/166; 428/182; 428/186; 428/323; 428/331
[58] Field of Search ............. 428/331, 166, 182, 186, 428/323, 134; 55/316, 319, 318, 387, 521, 524, 527, 528, 389; 128/296; 210/502, 506, 508; 162/158, 164

[56] References Cited

U.S. PATENT DOCUMENTS

| | | | |
|---|---|---|---|
| 2,955,067 | 10/1960 | McBurney | 210/502 |
| 3,091,550 | 5/1963 | Doying | 55/389 |
| 3,149,023 | 9/1964 | Bodendorf et al. | 162/135 |
| 3,266,973 | 8/1966 | Crowley | 210/502 |
| 3,327,859 | 6/1967 | Pall | 210/502 |
| 3,494,113 | 2/1970 | Kinney | 55/524 |
| 3,515,108 | 6/1970 | Deeter et al. | 55/316 |
| 3,572,014 | 3/1971 | Hansen | 55/316 |
| 3,577,710 | 5/1971 | Feldman | 55/318 |
| 3,664,095 | 5/1972 | Asker et al. | 210/502 |
| 3,727,384 | 4/1973 | Feldman | 55/316 |
| 3,747,303 | 7/1973 | Jordan | 55/316 |
| 3,807,149 | 4/1974 | Norback | 55/389 |

Primary Examiner—Paul J. Thibodeau
Attorney, Agent, or Firm—Stephen H. Cagle; Charles N. Shane, Jr.; W. G. Palmer

[57] ABSTRACT

This invention relates to a sorbtion paper which comprises a fibrous base paper material which is resiliently flexible and which is further characterized by being substantially free from loose, dusty sorbtion particles and by being substantially free of lumps and holes. Activated sorbtion particles are disbursed in the fibrous paper base material, the sorbtion particles being substantially uniformly dispersed throughout all dimensions of the base material and the activated sorbtion material being present in an amount of up to about 85% based on the weight of the base paper material. The activated sorbtion particles are characterized by a size of less than about 1,000 microns and an activation rating of less than about 250%. This invention further relates to sorbtion devices for use in combination with internal combustion engines and liquid body waste devices incorporating the above-recited sorbtion paper.

3 Claims, 12 Drawing Figures

ACTIVATED SORBTION PAPER AND PRODUCTS PRODUCED THEREBY

BACKGROUND OF THE INVENTION

1. Field of the Invention

This invention relates to sorbtion paper and sorbtion means for absorbing fumes and odors normally associated with internal combustion engines or body waste devices such as sanitary napkins and disposable diapers.

2. Prior Art a. Sorbtion Paper

The use of filter papers to filter both air and liquid components of various energy producing devices are well-known and represent a well-developed art. At the outset, it should be noted that the invention herein is not directed to a filter paper as is described in the prior art but rather this invention relates to a sorbtion paper. One essential distinction which must be noted is that in filter paper it is required that the material to be filtered actually physically pass through the filter paper primarily for the purpose of physically separating solid particles from a gaseous stream. In contrast, in the use of sorbtion paper such complete penetration of the paper substrate is not necessary and mere contact with the paper surface as in a laminar or turbulent flow pattern is all that is required to permit diffusion of gaseous components that a filter would allow to pass.

Furthermore, filter paper and the characteristics required thereof permits a paper density of only approximately 1.0 grams of paper per cubic inch while the apertured structure of the sorbtion paper and device of this invention permit a paper density of up to about 5.0 grams of paper per cubic inch of space. Even more beneficial, the sorbtion paper of this invention as a result of its characteristic better particulate retention permits approximately 30 percent greater activated particle loading than a correspondingly sized section of filter paper resulting in approximately six times the activated particle content per unit volume.

In the manufacture of filter papers of a conventional nature porosity of the final product is extremely important. Porosity of the final filter paper product is directly related to the required flow-through characteristics of the paper which are functionally necessary in filter paper. Previous attempts to incorporate activated material such as charcoal into the fibrous structure of the paper have suffered from this necessary porous nature of the filter paper product. In particular, it is necessary to use a binder material such as starch in the manufacture of filter paper to bind the charcoal particles to the fibrous structure of the base paper material. The result of the use of starch or similar binder materials in attempting to hold the charcoal or other particles in place is that the filter paper has a substantial amount of free, loose activated particulate material. This material is more free to rub off on or even contaminate the material being filtered than is the sorbtion paper of this invention. This is unacceptable in most filtration applications and therefore the use of activated material in filter paper has not previously been commercially successful where porosity of the filter paper is necessary to permit flow through of the stream being filtered.

Distinct from this, in the sorbtion paper of applicants' invention a latex type binder material and preferably an anionic polymeric emulsion is used to maintain the position of the activated particulate material. Thus even though the sorbtion paper of applicants' contains up to about 30 percent more activated material than is found in filter paper the final sorbtion paper product is substantially free from loose, dusty activated particulate material. The use of a starch or starch-like binder material results in an air filter paper which is substantially less flexible than the sorbtion paper product disclosed herein.

Furthermore, filter papers, especially those intended for gas phase applications such as automotive air filters, require high flow rates with minimum pressure drop. In order to permit such flow-through characteristics the fibers should be long and relatively stiff with minimum fibrillation or hydration, which are essentially means for increasing surface area. This permits large, uncluttered pores for easy air passage but also minimizes contact area between fibers thus leading to low paper strength. When binder materials such as starch are used to offset the low strength they must be non-film-forming to avoid blocking the filter pores.

In contrast to filter paper the sorbtion paper of this invention can be made with maximized sorption capabilities by using well fibrillated, or hydrated, fibers to provide good particle retention and good particle distribution. This is, of course, optional and fibers such as that used to make filter paper can be used to make sorbtion paper although the binders available for use in sorbtion paper can in some measure compensate for the general paper weakness. The use of film-forming binders as are described hereinbelow not only gives strength to the sorbtion paper itself but also provides a good matrix to prevent sorbtion particles from breaking loose and permits higher levels of sorbtion particle loading.

Further to the porosity characteristics of filter paper it can be shown that the internal bonding of sorbtion paper is substantially greater than the internal bonding characteristics of filter paper. As a result of this, devices, which are described hereinafter, cannot be made with filter paper and have the same necessary structural integrity that is found with sorbtion paper.

In its broadest scope this embodiment of the applicants' invention relates to a sorbtion paper and device which has been "loaded" with activated sorbtion particles to permit sorbtion and regeneration of the activated particles without the necessity for changing the paper or device. Other patents known to applicants and teaching the production of a loaded sheet and specifically a charcoal loaded sheet include U.S. Pat. No. 3,149,023 and its British equivalents, British Pat. No. 961,636; U.S. Pat. No. 3,253,978, and U.S. Pat. No. 3,594,993. While all of these carbon filled sheet patents relate generally to filtration type charcoal loaded paper the distinctions therefrom are numerous and have been pointed out hereinabove. Specifically, the carbon paper of the prior art is generally specific to filtration means and is not correspondingly related to sorbtion means. In this regard it should be once again emphasized that the sorbtion paper of applicants' invention does not require penetration and flow through characteristics which are required for the functioning of known filtration elements.

b. Sorbtion Paper For Use in Combination with Internal Combustion Engines

Hence the substantial body of prior art which relates to filter papers is not equally applicable to sorbtion papers as among other things the mechanism for cleansing the particular gas or liquid is substantially different. In this regard, one embodiment of the present invention relates generally to a sorbtion medium and is directed, more particularly, to a novel sorbtion paper having improved and unique properties for use as a gas sorbtion medium such as in combination with air filters for the air intake system of internal combustion engines.

While the sorbtion paper of the present invention is not limited to use in air filtration systems for internal combustion engines, this use will be particularly described herein because it emphasizes the problems encountered in providing a suitable air sorbtion medium for use in conjunction with air filtration systems and further emphasizes the unique characteristics of the paper and paper devices of this embodiment of the present invention.

In this preferred embodiment the invention relates to a sorbtion device to control hydrocarbon evaporation losses from automobiles. More particularly, the sorbtion device controls hydrocarbon evaporative loss from the carburetor and/or fuel systems of automobiles, trucks and other motorized vehicles.

It has long been established that automobiles constitute a significant source of atmospheric pollution and contamination, leading to the smog problem in many cities. While the bulk of polluting emissions come from the automobile exhaust in the form of unburned hydrocarbons and nitrogen oxides, unburned hydrocarbons also pass into the atmosphere from the carburetor and fuel systems by evaporation. While the amount may not seem to be great enough in one automobile to cause the owner to think he is suffering from this waste, the compounding of the polluting effect by millions of automobiles has resulted in major problems. In its preferred embodiment the present invention is intended to solve this problem by keeping the unburned hydrocarbons escaping the automobile carburation and fuel systems within acceptable limits.

While this has been recognized as a major problem, earlier attempts to solve this problem have generally resulted in overly sophisticated devices and ones which have in some instances proven to be not commercially practical. See for example U.S. Pat. No. 3,191,587. The most common solution to this well-known problem has been the use of air filters in combination with carburation systems in automobiles. This is exemplified by the following patents, U.S. Pat. Nos. 3,505,795; 3,513,643; and 3,747,303. Other patents known to applicants which have shown other somewhat more elaborate devices, all of which depend ultimately on filter paper would include U.S. Pat. No. 3,628,517; 3,646,731, and 3,730,158.

While other patents such as U.S. Pat. No. 3,747,303 mention the use of certain activated particles such as carbon for use with filtration means the sorbtion paper and device of applicants are thought to be novel and to show unique characteristics for performing desired sorbtion functions when used in conjunction with filtration means as for example in an internal combustion engine.

c. Body Waste Devices

A second preferred embodiment of this invention relates to the use of the activated sorbtion paper of this invention in combination with body waste devices such as sanitary napkins, disposable diapers and the like. In this particular embodiment of the invention it is not necessary that the activated sorbtion paper be configured as an apertured structure as the paper itself provides the most convenient insert for such body waste devices. However, any desired configuration which is acceptable to the overall product design of the body waste device is possible.

It is well known that some menstruating females emit odorous menstrual fluids. Emitted fluids can also rapidly form odorous products on further proteolytic reaction. It is established that some of the most perceptible odors are due to chemically basic amine type compounds, which are volatile. The characteristic amine type odors are embarrassing to menstruating females.

The urine impregnated diapers of infants are well known for having and developing an ammonical odor on storage or on extended periods of use such as overnight. The widespread use of single use, disposable baby diapers is restricted by the persistant ammonical odor of the discarded, used diapers, prior to their final disposal outside the baby's household. In addition, the ammonical urine products can induce a common rash on the baby's torso, due to the alkaline pH of the urine in persistent contact with the baby's skin.

The improved body waste device of this invention alleviates the odor problems outlined above by providing a sorbtion paper insert which absorbs and/or adsorbs many of the undesirable odors characteristic of body waste devices such as sanitary napkins and diapers. Body waste devices of this type are uniformly characterized by being disposable and hence sorbtion paper such as will be described hereinafter which does not chemically react with, modify or deactivate the undesirable fumes can be advantageously used.

Previous attempts to deal with these problems in body waste devices have generally involved an attempt to chemically modify the material used to make the body waste device so as to neutralize the odors present. See for example U.S. Pat. No. 3,340,875 and U.S. Pat. No. 3,794,934. Other approaches to this problem have involved the use of physical barriers and the like to attempt to confine the odors. These previous attempts to deodorize body waste products have been largely commercially unsuccessful for both technical and commercial reasons. Other known prior art which is of interest to this embodiment of this invention includes: U.S. Pat. No. 1,773,956; U.S. Pat. No. 2,960,089; U.S. Pat. No. 3,036,573; U.S. Pat. No. 3,340,875; U.S. Pat. No. 3,430,629; U.S. Pat. No. 3,779,246; and U.S. Pat. No. 3,794,034.

Therefore, it is an object of this invention to provide a sorbtion paper which will adsorb and adsorb vapors and fumes on contact.

It is a further object of this invention to provide a sorbtion paper device which is configured so as to provide maximum flow-through characteristics through channels which permit maximum absorption and adsorption of noxious fumes such as hydrocarbons produced by an automobile's internal combustion engine.

A still further object of this invention is to provide a particular sorbtion device for use in combination with filtration means in an internal combustion engine.

An additional object of this invention is to provide a sorbtion paper inert for use in combination with body waste devices such as sanitary napkins and disposable diapers. These and other object of this invention become apparent from the following description of the preferred embodiments.

SUMMARY OF THE INVENTION

This invention relates to a sorbtion paper which comprises a fibrous base paper material which is resiliently flexible and which is further characterized by being substantially free from loose, dusty sorbtion particles and by being substantially free of lumps and holes. Activated sorbtion particles are disbursed in the fibrous paper base material, the sorbtion particles being substantially uniformly dispersed throughout all dimensions of the base material and the activated sorbtion material being present in an amount of up to about 85% based on the weight of the base paper material. The activated sorbtion particles are characterized by a size of less than about 1,000 microns and an activation rating of less than about 250%. This invention further relates to sorbtion devices for use in combination with internal combustion engines and liquid body waste devices incorporating the above-recited sorbtion paper.

DETAILED DESCRIPTION OF THE PREFERRED EMBODIMENTS

For the purposes of promoting an understanding of the principals of the invention, reference will now be made to the embodiments illustrated in the drawings and specific language will be used to describe the same. It will nevertheless be understood that no limitation of the scope of the invention is thereby intended, such alterations and further modifications in the illustrated device, and such further application of the principals of the invention as illustrated therein and contemplated as would normally occur to one skilled in the art to which the invention relates.

In describing the sorbtion paper of this invention it should be noted that various fibers and mixtures of fibers may be employed in the formulation of the sorbtion paper of the preset invention including but not limited to natural cellulosic fibers, jute, bleached or unbleached kraft, caroa, sisal, kozu; synthetic fibers such as viscos and acetate rayon, polyamide, vinyl acetate-vinyl chloride copolymer and polyester (dacron, E. I. DuPont de Memoirs & Co., Wilmington, Del.); and inorganic fibers such as glass, quartz and ceramics including fused alumina-silica mixtures.

Natural cellulosic fibers are preferred for most applications of the sorbtion paper of this invention in that the binder added functions primarily to retain particulate material and substantially no binder is necessary to actually give strength to the sheet itself. As has been pointed out hereinbefore the internal bond strength of the fibrous material and the use of latex binders are an important advantage enjoyed by the sorbtion paper product of this invention in distinction to the filter papers shown by the prior art. If so desired, however, a small amount of an added binder material can also be incorporated to enhance the bond formed by the cellulosic material.

Synthetic organic fibers and inorganic fibers may be desirable for applications where resistance to high temperatures or corrosive conditions are necessary. The synthetic and inorganic fibers may also be mixed with each other, and they may be used singly or jointly in combination with the natural cellulosic fibers to provide sheets incorporating advantageous properties of the cellulosic fibers. The particular fibrous makeup is dependent on the end use to which the sorbtion paper is to be placed.

The fibers are generally of a paper making length, i.e. predominately of about 1/32 inch to about ⅜ inch and the synthetic or inorganic fibers may even be longer than one inch depending on the dispersability of the fibers to provide an aqueous slurry. The synthetic and inorganic fibers are unhydrated but the natural cellulosic fibers may be beaten and hydrated, particularly for increasing the strength of the sheet.

Other characteristics of the sorbtion paper product of this invention are resilient flexibility; being substantially free of loose activated sorbtion particles and being substantially free of lumps and holes.

The resilient flexibility characteristic of the sorbtion paper product is necessary to permit a configuration of the base paper into any of a large variety of tunneled or apertured structures or to allow contouring necessary for use in body waste devices. The tunneled structures are most advantageous for supplying the maximum amount of surface to the air flow containing the noxious fumes, i.e. hydrocarbons. As has been pointed out hereinbefore filter papers using starch or starchlike material as a binder do not possess the structural integrity or flexability to be made into devices which are described and shown herein.

Furthermore, it is necessary that the sorbtion paper of this invention not only be resiliently flexible but at the same time the surface characteristics of the paper must not be impeded or coated in any fashion which will prevent penetration and adsorption and absorption of noxious fumes or odors. In this regard filter paper is distinct from sorbtion paper in that the filter paper must be porous and aligned in a fashion which permits free flow or substantially free flow of a stream of gas therethrough. In contrast to this, the sorbtion paper of applicants' invention requires only an exposed surface area which permits adsorption and absorption of fumes. The ability to freely flow through the thickness of the sorbtion paper is not necessary. In certain applications such as automobile air filtration this contact functional characteristic of the sorbtion paper device is critically important as the pressure drops normally found in using filter paper is either not present or is substantially reduced.

A further characteristic of the sorbtion paper of this invention is the substantial absence of loose, dusty sorbtion particles. As will be more fully described hereinafter the sorbtion particles can be any of a number of known materials. Included in these materials are activated carbon, activated silica gel, polymeric absorbance materials, molecular sieves (for an explanation see U.S. Pat. No. 3,382,141) ion exchange resins and other carbonaceous absorbance materials. It is essential that these materials be supplied in particulate form. As such it is further important that the particulate form be substantially completely embedded in the fibrous structure of the sorbtion paper sheet. The reasons for such a requirement appears obvious. In the first instance activated carbon is quite messy and would be likely to rub off or otherwise be removed from the paper which is totally unacceptable in any body waste device. This would limit to a small extent the sorbtion activity of the paper as well as adversely affecting the surface characteristic of the paper.

Furthermore, in one of the preferred applications of the sorbtion paper product of this invention, namely a sorbtion device for use in combination with filtration means found in the carburation and fuel systems of an automobile engine, the activated sorbtion particles would not be tolerated as they could well find their way into the moving portions of the automobile engine and cause substantial damage thereto.

The prevention of free, loose activated particulate material is largely a function of the particular binder material used. As has been stated hereinbefore filter papers have been made for the most part with the use of starch or starch-like binder materials. Sorbtion paper on the other hand is made using a latex type binder and preferably an anion polymeric emulsion of such latex material. Latex materials which have been shown to be viable include: polyvinyl chloride copolymer, acrylics, vinylidene chlorides, acrylonitriles, vinyl acetates, polybutadiene, styrene butadiene, phenolic resins and combinations thereof. It should be understood that this list represents only a portion of the latex binders which are useful in the manufacture of sorbtion paper. The use of latex binders not only results in the substantial elimination of free, loose particulate material but also results in a strong internal bond and a paper product which has improved structural integrity. It is necessary, however, that the binder material when used be a solution, emulsion or dispersion capable of being codispersed with the sorbtion particles and precipitated, flocced, coagulated, etc. together with the sorbtion particles. Although most of the known useful binder emulsions are anionics in nature cationic or non-ionic materials can be used as long as they meet the above-requirements.

It has further been pointed out that a lack of lumps and holes is important in the sorbtion paper product of this invention. One of the primary adverse effects of lumps would be the formation of an impediment to processing such as corrugating, etc. The presence of large particles would also cause problems when working loose from the paper. This risk of damage to processing machinery and internal combustion engines is substantial with large carbon particles. This would not be acceptable in a product such as sorbtion paper. Holes which may be present in the paper of this invention are also not acceptable as they would provide basis for tearing and for decreased performance characteristics of the various sorbtion devices made from the sorbtion paper of this invention.

In one of the preferred embodiments of this invention activated carbon particles 10 are used as the sorbtion material and are employed in amounts of up to about 85% by weight of the finished sorbtion paper sheet 11. Although activated carbon particles 10 of up to 1,000 micron diameter may be utilized a size of from about 1 micron to about 300 microns on average is preferred and a size of from about 5 microns to about 75 microns is most desirably used for optimum activated carbon particle retention.

One form of carbon particle which has been shown to be adequate is "Columbia" activated carbon as supplied by the Union Carbide Corporation of New York, N.Y. Characteristics of the activated carbon which are found advantageous are an extended surface area and good capillary structure. The particular functioning ability of individual carbon particles is controlled by factors such as temperature, vapor concentration, composition of vapors, and the grade of activated carbon.

Specifically, lower temperatures and higher vapor concentrations favor higher levels of absorption on the carbon particles. Conversely, higher temperatures and lower vapor concentrations favor lower loading levels. The amount of hydrocarbon vapor adsorbed and desorbed for a given set of operating conditions by a carbon material is called the "working capacity". It is commonly expressed as pounds of vapor per hundred pounds of activated carbon. The absorption process releases heat which is greatest on the first cycle with new activated carbon. Since subsequent cycles involve only a fraction of the initial absorption, the heat of the adsorption will be much smaller.

In defining and evaluating activated carbon the standard which is used is the carbon tetrachloride activity scale. The carbon tetrachloride activity is the percent by weight of carbon tetrachloride adsorbed at 25° C. from dry air saturated with this vapor at 0° C. This value can also be used as a relative indication of the adsorptive capacity of activated carbons. In this regard an activated carbon rating on the carbon tetrachloride activity scale of from about 10% up to and including about 250% is most desired. An activity rating of about 30% to about 150% is preferred and an activity rating of 50% to about 125% is more preferred.

The carbon particle 10 content of the sorbtion paper 11 of this invention may be varied over a wide range and as indicated above up to as much as about 85% by weight of the base sheet may be used. Generally, however, amounts in excess of 85% by weight will tend to produce some rub-off. For the activated carbon sorbtion sheet of this invention the carbon content should be within the range of from about 15% to about 75% by weight and preferably from about 25% to about 70%.

Figure 7:
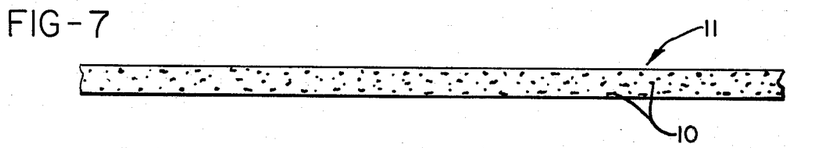
FIG. 7 is a cross-sectional view of the sorbtion paper of this invention showing schematically the distribution of activated particulate material.
Figure 8:
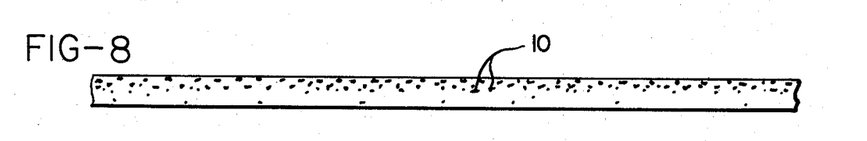
FIG. 8 is a cross-sectional view similar to FIG. 7 showing the particulate material distribution typical of known filter papers.

Furthermore, incorporating the activated carbon or other sorbtion particles into the fibrous substrate it is necessary that the carbon particles be substantially uniformly distributed as is shown by FIG. 7. This is in contrast to many filter papers and other types of papers' teachings (see FIG. 8) wherein it is specifically desired that a substantially greater proportion of the active materials be gathered close to one surface or the other. Such is not the case in applicants' invention and a uniform distribution of the particulate matter throughout the paper or the fibrous substrate is desired. This provides the basis for uniform adsorption and absorption on both exposed surfaces of the sorbtion paper substrate.

Figure 1:
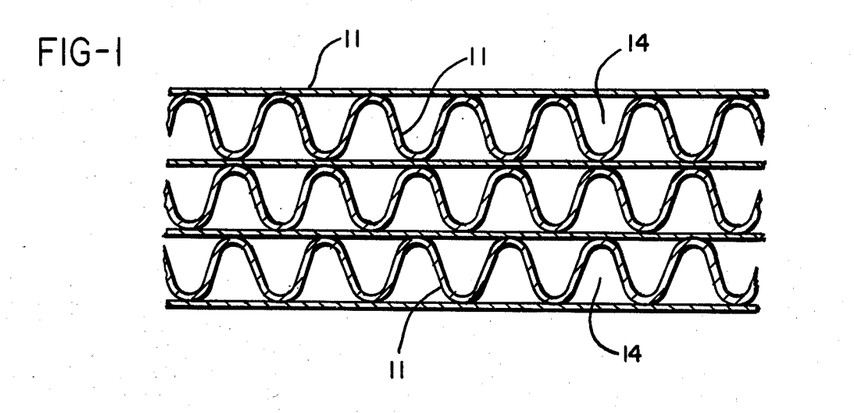
FIG. 1 is a cross-sectional view of a particular configuration of the sorbtion paper of this invention corrugated in parallel rows.
Figure 2:
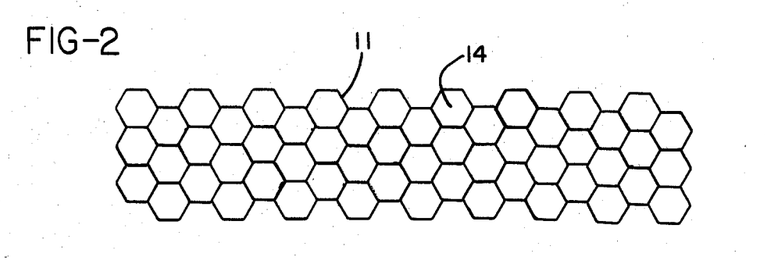
FIG. 2 is a cross-sectional view of an alternate configuration of the sorbtion paper of this invention arranged in an apertured honeycombed fashion.
Figure 3:
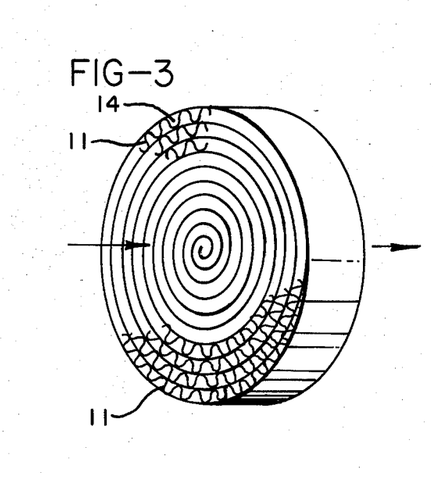
FIGS. 3 and 4 are cross-sectional perspective views of a sorbtion device of this invention demonstrating the direction of a gaseous stream flow.
Figure 4:
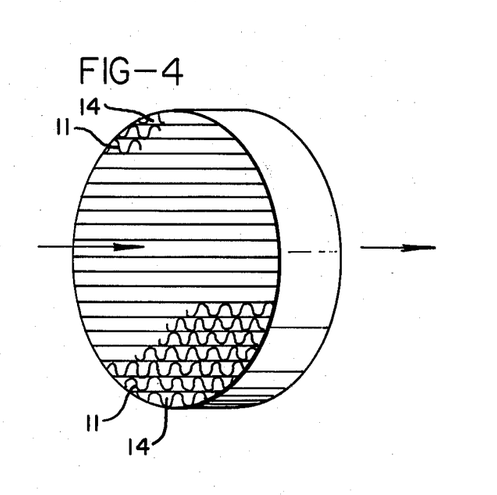

As has been developed supra the sorbtion paper of this invention has numerous applications, i.e. any process wherein a source of absorption and adsorption is required to eliminate fumes or noxious odors caused by fumes and especially if that source is to be regenerable. In this regard the sorbtion paper of this invention can be best used in the internal combustion engine application by configuring the product into a tunneled construction. In this regard reference will now be made to FIGS. 1 through 4. Specifically, it is noted that structures such as are shown in FIGS. 1 and 2 are preferred as the maximum surface area possible is permitted in the smallest area and is most conveniently adapted to standard manufacturing techniques. The configurations such as are shown in FIGS. 1 through 4 shall hereinafter be sometimes referred to as the "apertured structure". By apertured structure it is meant that a plurality of apertures 14, each of the apertures being formed by the configuration of sorbtion paper 11 of this invention, are present in a structure which permits a free flow of air in either a laminar or turbulent fashion.

The preferred aperture density for sorbtion devices such as those shown in FIGS. 1 through 4 is from about 25 apertures per square inch to about 400 apertures per square inch when measured as a cross-sectional area. However, it should be noted that these aperture densities refer to flute sizes commonly used in corrugating materials. While these sizes (A to E flutes) are preferred, this invention may be practiced equally well with larger or smaller flute sizes, depending on the particular end use.

Figure 5:
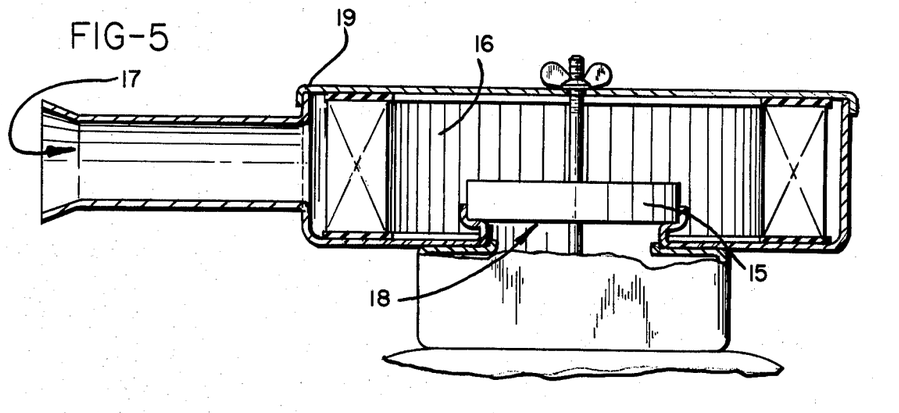
FIG. 5 is a cross-sectional view of one embodiment of a sorbtion device of this invention in combination with automobile air filtration and carburation means.
Figure 6:
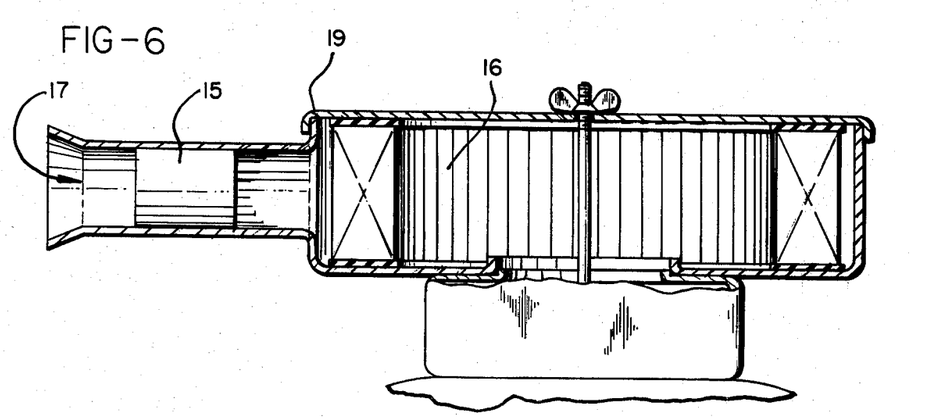
FIG. 6 is a cross-sectional view of a second embodiment of a sorbtion device of this invention in combination with automobile air filtration and carburation means.

Referring now to FIGS. 5 and 6, it has long been recognized that it is desirable to filter the air intake of internal combustion engines to remove dust and other foreign particles prior to carburization, etc. The usual practice heretofore has been to utilize air filters of the fluted paper type despite the fact that such filters are not substantial in construction and require frequent maintenance and/or replacement. It has been proposed heretofore to use other types of filters, but no commercially acceptable substitute has been found which will meet the stringent requirements of this specific use. For example, an air filtering medium for use with internal combustion engines must have a high degree of permeability in order that within reasonable size limitations it will admit a high volume of air (of the order of 100 cubic feet per minute) without undesirable pressure drop and at the same time it must accomplish a satisfactory filtering and cleaning action and yet not become so rapidly plugged up with foreign matter removed from the air so that it will have a short service life necessitating frequent replacement.

In the most preferred embodiment of this invention the sorbtion device 15 is placed in cooperating relationship with air filtration means 16 normally found in the carburation or fuel systems of automobile engines. Specifically, it is known to reduce the emission of hydrocarbon vapors from fuels to the ambient atmosphere by venting the reservoirs of such fuel, such as the float bowl section of a carburetor or, to the air mixing chamber of the carburetor where such hydrocarbon vapors may be mixed with air and burned in the engine. However, when the engine does not operate, such vapors unless otherwise adsorbed could escape to the atmosphere. In this regard it is necessary to effect the adsorption of these vapors to prevent such atmospheric escape.

The sorbtion device 15 and sorbtion paper 11 of this invention may therefore be placed in a convenient location between the air inlet 17 and filter element 16 or between the filter element 16 and the intake assembly for the carburetor see FIGS. 6 and 5 respectively. It is necessary however that the sorbtion device not interfer with the cleaning of the ambient air filter nor should it introduce pressure drops affecting the conduction of clean air to the carburetor. Moreover, to avoid being broken into its composite particles and being drawn into the intake manifold of the engine, the sorbtion device should not be free to vibrate around the interior of its housing. Furthermore, to reduce part inventories and to facilitate servicing, it is desirable to integrate the sorbtion device 15 with the conventional air filter element 19 and to place the resulting sorbtion device 15 in a position in said element to permit the most efficient use of the surface area of the sorbtion paper. In the alternative the sorbtion device 15 can be placed separately in the standard air filter housing.

An important aspect of this invention and one which is substantially distinct from filter papers is that the sorbtion paper acts to adsorb and absorb excess fuel vapors when they are conveyed into the sorbtion devices 15 as shown in FIGS. 5 and 6. The important point is that the sorbtion paper and the carbon particles contained therein are purged of these vapors by the flow of fresh air through the air filters 16 and the sorbtion device 15 and into the carburetor during normal operation of the engine. That is, when the engine has been restarted, the suction again will draw air through the air cleaner assembly including the sorbtion device from the inlet duct in the normal manner. This will create a pressure differential between opposite ends of the air filtration assembly causing fresh air to flow through the sorbtion device and into the carburetor to purge the sorbtion device of the adsorbed and absorbed fuel vapors. In this fashion the sorbtion device is regenerated and does not require replacement for chemical reasons. These vapors once they are purged from the sorbtion device pass through into the carburetor and are burned in the engine.

In specifically designing the sorbtion device for use in the products of this invention the aperture density is of course an important consideration. In this regard commercial and practical reasons lend themselves to support a range of from about 25 apertures per square inch to about 400 apertures per square inch depending on the particular application as the optimum number of apertures of the sorbtion device.

Figure 9:
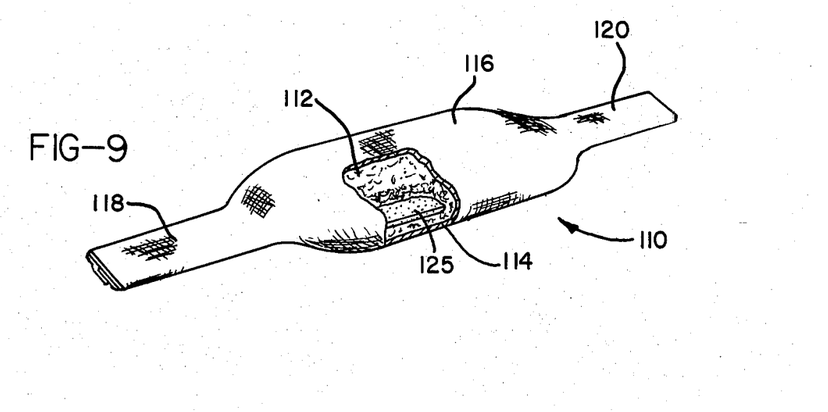
FIG. 9 is a cross-sectional view of a sanitary napkin product with an activated sorbtion paper insert.
Figure 10:
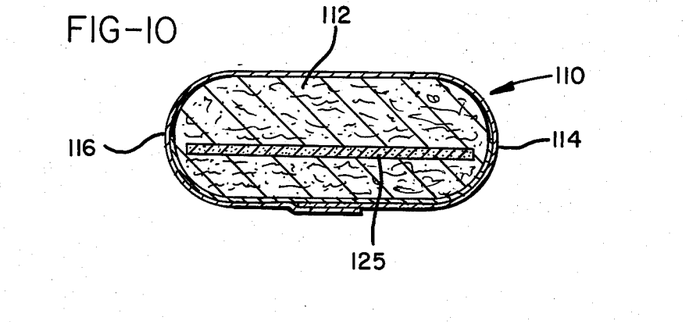
FIG. 10 is a top plan view with a portion thereof sectioned showing the sanitary napkin of FIG. 9.

An alternate embodiment of this invention involves the incorporation of the activated sorbtion paper of this invention into the construction of a body waste device such as a sanitary napkin or paper diaper. This embodiment of the invention is generally illustrated by FIGS. 9 through 12. Referring now to FIGS. 9 and 10 a typical construction of a sanitary napkin is shown. In particular as is shown in the drawing a sanitary napkin 110 comprising an absorbent pad 112, the lower face and portion of the sides of which are protected by a moisture-impermeable film 114. The absorbent pad-film 114 assembly is overwrapped with an outer cover 116 having end extensions 118, 120 by means of which the napkin can be affixed to a sanitary belt.

The absorbent pad 112 can comprise any suitable absorbent material such as culminated wood pulp fibers, creped cellulose wadding or the like. The size and shape of the pad can be varied without effect on the present invention. The pad 112, can for example, be substantially rectangular in horizontal and vertical section, having a width of two and one-half inches, a length of eight inches, a thickness of one inch and weigh approximately eleven grams.

The film 114, if used, can comprise any suitable and compliant moisture impermeable membrane. It has been found that one-half mil polyethylene film having a length approximating or somewhat greater than that of the pad 112 and a width slightly greater than the width of the pad 112, for example about three and one-quarter inches wide can be used with a pad 112 sized as described above. The purpose of the film 114 is to prevent strike through menses which has penetrated the full thickness of the pad 112. While the film 114 can ordinarily be made to cover all of the pad 112 with the exception of a portion to be placed adjacent the vulva of the consumer in use, when used with napkins 110 of the present invention it should be preferably cover as little as possible of the body contacting areas because such materials when so positioned reduce air circulation and make the napkin 110 feel hot and uncomfortable.

The outer cover 116 has a width sufficient to encircle the transverse section of the napkin with slight overlap permitting the longitudinal edges of the fabric to be united by adhesives. The fabric can be selected from any satisfactory materials such as gauze, knitted scrims or bonded non-woven materials, apertured or non-apertured. Preferably, the fabric is white, porous, fluid pervious, absorptive, soft, smooth surfaced, strong in at least one direction and resistant to pilling. Such a fabric will look and feel good to a consumer as well as perform satisfactorily as an outer cover 116 when practising the present invention.

The odor associated with active use of the napkin of this invention have been well-known as is described hereinabove. However, the solution of this problem is made extremely difficult due to the delicate nature of use and application of this particular product. In this regard the sorbtion paper device 125 of this embodiment of this invention is used as an insert as is shown in FIGS. 9 and 10. Acutal placement of the device 125 is optional with the napking manufacturer although a placement intermediate the width of the absorbent pad 112 is preferred. In this fashion when the pad is actually used the odor associated with the menses is adsorbed and absorbed by the sorbtion paper 125 to provide a more hygenically acceptable sanitary napkin product.

It is of special interest to note that in the process of manufacturing sanitary napkins such as is shown in FIGS. 9 and 10 it is most economical that the napkins be produced in a continuous fashion. As can be appreciated, this does not lend itself to convenient insertion of sorbtion paper devices. Therefore, it is of special significance that the sorbtion paper 125 of this embodiment of this invention can be added in roll form to the continuously produced sanitary napkin product. In order to accomplish this it is merely necessary that the roll of sorbtion paper be sized appropriate to fit within the boundaries of the sanitary napkin product. Then, as the sanitary napkin is produced, folded and otherwise manufactured the addition of the sorbtion paper becomes merely one step incorporated into the overall continuous sanitary napkin production.

In actual use, the end extensions 118 and 120 of the napkin of this invention can be fastened to a sanitary belt with a portion thereof adjacent the vulva and thus positioned to receive the flow of menses. The fluid penetrates the outer cover 116 through its thickness in area and is absorbed by pad 112. While the menses is retained by the pad 112 the odor normally associated therewith will be substantially adsorbed and absorbed by the sorbtion paper device 125 located in the pad 112.

A second body waste device for which the sorbtion paper of this invention has application is the disposable diaper. As is shown in particular by FIGS. 11 and 12 the diaper assembly 210, when fully opened and layed out flat, comprises, in order, fibrous facing layer 216 adapted to be positioned adjacent skin of an infant, absorbent fibrous pad, or batt 214, water imperious sheet 212 and finally an outermost layer 213 of fibrous material. Fibrous layers 213 and 216 are generally rectangular in shape, equal in dimension, and coterminous with backing sheet 212. Batt 214 is also rectangular in shape, but smaller than sheet 212 and layer 216, and disposed centrally thereof. The marginal portions 212b and 216b of sheet 212 and facing layer 216, respectively, are in face to face engagement with one another, and outermost layer 213 is in face to face engagement with sheet 212 throughout the interface therebetween.

Figure 11:
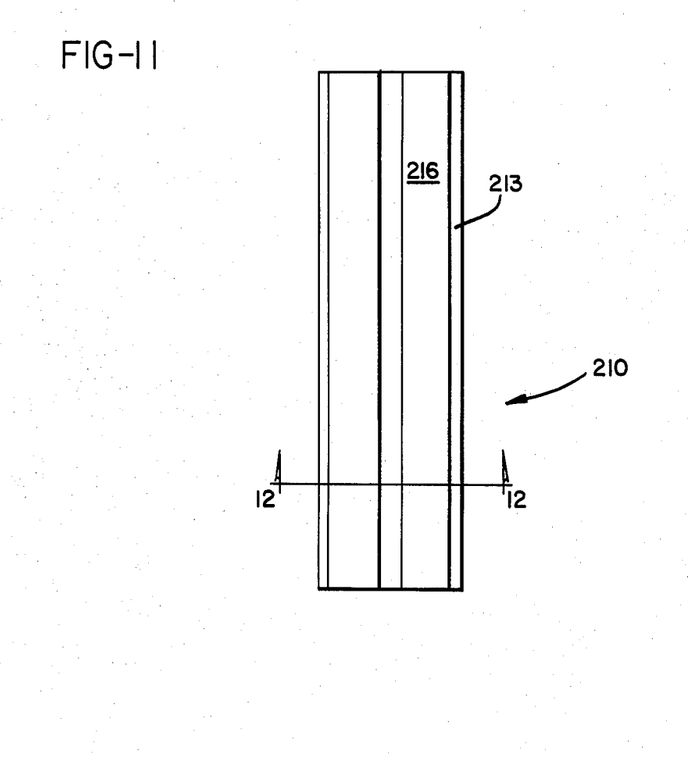
FIG. 11 is a cross sectional view of a paper diaper product with an activated sorbtion insert.
Figure 12:
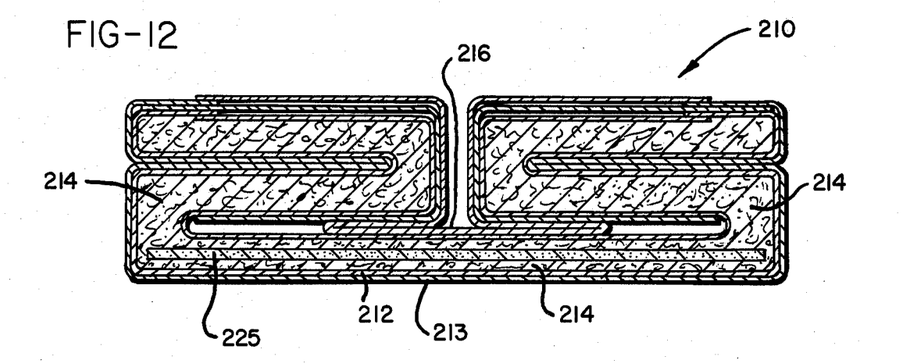
FIG. 12 is a top plan view with a portion thereof sectioned showing the disposable diaper of FIG. 11.

Sheet 212 is formed of a flexible, moisture impervious material, preferably thermoplastic, and since sheet 212 is enclosed within the interior of the diaper, it may be formed of a thinner gage material than is necessary in other constructions when the sheet is relied upon as the main component to provide strength and stability to a diaper.

Batt 214 is formed of loosely compacted short cellulose piped fibers, such as wood pulp fibers, or cotton linters, or mixtures thereof, which are primarily held together by interfiber bonds requiring no added adhesive, as is known in the art. Briefly, this batt is a low bulk density coherent web of loosely compacted cellulose fibers, preferable culminated wood pulp fibers in the form of so called "fluff".

Facing layer 216 is made up of a mixture of fibers consisting predominately of short cellulosic fibers such as wood pulp fibers for cotton linters, in amounts of about 75 percent to about 98 percent, the balance being textile lint fibers such as rayon. Short cellulosic fibers such as wood pulp fibers or cotton linters are substantially less expensive than textile length cellulosic fibers such as cotton and rayon, and this low cost is a factor in reducing the cost of the facing layer component of the diaper of this invention.

As above in the application of the sorbtion paper of this invention to sanitary napkins a sorbtion device is placed in the fluff portion of the disposable diaper to retain odors especially the ammonia like odors created by the deposit of urine in said diaper by an infant. As is shown in FIGS. 11 and 12 a sorbtion device 225 comprising a section of sorbtion paper is included in the fluff portion of the disposable diaper. The particular configuration of the sorbtion paper device 225 or the placement or such sorbtion paper device 225 in the diaper itself is a matter of choice and is not part of this invention. However, the placement shown in FIGS. 11 and 12 corresponds precisely to the most advantageous placement to permit continuous manufacture of paper diapers. In this regard the art is quite well developed relating to disposable diapers and processes for their manufacture. As can be appreciated there are a number of known products and processes all of which have applicability to combination with the sorbtion paper device of this invention.

Having described several embodiments of the present invention, it is understood that the specific terms and examples are employed in a descriptive sense only and not for purposes of limitation. Other embodiments of the invention, modifications thereof, and alternatives thereto may be used. We therefore aim in the appended claims to cover such modifications and changes as fall within the true spirit and scope of our invention.

What is claimed:

1. A sorbtion device comprising the combination of:
   (a) a fibrous paper base material, said base material being resiliently flexible and being characterized by:
      (i) being substantially free of loose, activated sorbtion particles;
      (ii) being substantially free of lumps and holes;
   (b) activated sorbtion particles suitable for sorbtion of gaseous materials being dispersed in said fibrous paper base material, said sorbtion particles being selected from the group consisting of activated charcoal and activated silica, said activated sorbtion particles being substantially uniformly dispersed throughout all dimensions of said fibrous paper base material, said activated sorbtion particles being present in an amount of up to about 85 percent based on the weight of said base paper material, said particles being characterized by:
      (i) a particle size of less than about 1000 microns;
      (ii) an activation rating of less than about 250 percent;
      (iii) the ability to be self-regenerable;
   (c) a latex type binder material to bind said activated sorbtion particles to said fibrous base paper material, said binder material being substantially free of starch, said binder material being compatible with the sorbtion activity of said sorbtion paper;
   (d) said fibrous paper base material being configured as an apertured structure characterized by a cross-sectional aperture density of from about 25 per square inch to about 400 per square inch; said apertured structure being further characterized by creating substantially linear, uniform parallel flow tunnels for gaseous streams passing through said apertures; said apertured structure being sized appropriately for lodging in the housing of air filtration means found on internal combustion engines; and
   (e) air filtration means usable in combination with said apertured structure to provide an air filtration system for use in conjunction with an internal combustion engine whereby air entering and leaving said internal combustion engine is subjected to filtration, absorption and adsorbtion forces.

2. The sorbtion device of claim 1 wherein said latex type binder is an anionic polymeric material selected from the group consisting of: polyvinyl chloride copolymers, acrylics, vinylidene chlorides, acrylonitriles, vinyl acetates, styrene butadiene, polybutadiene, phenolic resins and combinations thereof.

3. A sorbtion device comprising the combination of:
   (a) a fibrous paper base material, said base material being resiliently flexible and being characterized by:
      (i) being substantially free of loose, activated sorbtion particles;
      (ii) being substantially free of lumps and holes;
   (b) activated sorbtion particles suitable for sorbtion of gaseous materials being dispersed in said fibrous paper base material, said activated sorbtion particles being selected from the group consisting of: activated charcoal and activated silica, said activated sorbtion particles being substantially uniformly dispersed throughout all dimensions of said fibrous paper base material, said activated sorbtion particles being present in an amount of up to about 85 percent based on the weight of said base paper material, said particles being characterized by:
      (i) a particle size of less than about 1000 microns;
      (ii) an activation rating of less than about 250 percent;
      (iii) the ability to be self-regenerable;
   (c) a binder material to bind said activated sorbtion particles to said fibrous base paper material, said binder material being substantially free of starch, said binder material being a latex material of the anionic polymer type selected from the group consisting of: polyvinyl chloride copolymers, acrylics, vinylidene chlorides, acrylonitrites, vinyl acetates, styrene butadiene, polybutadiene, phenolic resins and combinations thereof, said binder material being compatible with the sorbtion activity of said sorbtion device;
   (d) said fibrous paper base material being configured as an apertured structure characterized by a cross-sectional aperture density of from about 25 per square inch to about 400 per square inch; said apertured structure being further characterized by creating substantially linear, uniform parallel flow tunnels for gaseous streams passing through said apertures; said apertured structure being sized appropriately for lodging in the housing of air filtration means found on internal combustion engines; and
   (e) air filtration means usable in combination with said apertured structure to provide an air filtration system for use in conjunction with an internal combustion engine whereby air entering and leaving said internal combustion engine is subjected to filtration, absorption and adsorbtion forces.

* * * * *